US00PP27059P3

(12) United States Plant Patent
Evers

(10) Patent No.: US PP27,059 P3
(45) Date of Patent: Aug. 16, 2016

(54) CLIMBING ROSE PLANT NAMED 'TAN07891'

(50) Latin Name: ***Rosa* L.**
Varietal Denomination: Tan07891

(71) Applicant: Rosen Tantau KG, Uetersen (DE)

(72) Inventor: Christian Evers, Uetersen (DE)

(73) Assignee: Rosen Tantau KG, Uetersen (DE)

( * ) Notice: Subject to any disclaimer, the term of this patent is extended or adjusted under 35 U.S.C. 154(b) by 79 days.

(21) Appl. No.: 14/544,002

(22) Filed: Nov. 12, 2014

(65) Prior Publication Data

US 2016/0135340 P1 May 12, 2016

(51) Int. Cl.
*A01H 5/02* (2006.01)

(52) U.S. Cl.
USPC ..... Plt./114

(58) Field of Classification Search
USPC ..... Plt./114
See application file for complete search history.

(56) References Cited

PUBLICATIONS

UPOV hit on a climbing rose plant denominated 'TAN07891', QZ PBR 40086, published Aug. 16, 2013.*

* cited by examiner

*Primary Examiner* — Anne Grunberg
(74) *Attorney, Agent, or Firm* — Klarquist Sparkman, LLP

(57) ABSTRACT

A relatively tall mini-climbing rose plant is disclosed that has many branches and many doubles flowers, and flowers that are pink and lack fragrance.

7 Drawing Sheets

Genus and species: *Rosa* L.
Variety denomination: 'TAN07891'.

ORIGIN OF THE INVENTION

The present invention relates to a new and distinct variety of a climbing rose plant named 'Tan07891' which was originated by me by crossing the variety 'Hobby RT92165' (seed parent, unpatented), with the variety 'Leonardo da Vinci' (pollen parent, unpatented).

BACKGROUND OF THE INVENTION

The primary objective of this breeding was to produce a new climbing rose variety.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. A relatively tall mini-climbing rose plant.
2. A climbing rose plant that produces many branches and many double flowers.
3. A climbing rose plant with pink flowers.
4. Flowers that lack fragrance.
5. A climbing rose plant with many umbels.

Asexual reproduction of this new variety by cuttings and budding, as performed at Uetersen, Germany, shows that the foregoing and all other characteristics and distinctions come true to form and are established and transmitted through succeeding propagations. The first asexual propagation of this new variety was performed in 2008.

COMPARISON WITH PARENTS

Compared to its female parent, 'Hobby RT92165', which typically grows to 40 to 50 cm, 'Tan07891' grows higher (150 to 200 cm). Compared to its female parent, which has a Dark Pink RHS 63B flower color, 'Tan07891' has a Pink RHS 65A flower color. Compared to its female parent, the flower shape of 'Tan07891' is strong double, the female parent's flower shape is single. Compared to its male parent, 'Leonardo da Vinci', which has a darker pink color and typically grows to 60 cm, 'Tan07891' is lighter pink and grows higher (150 to 200 cm).

COMPARISON WITH SIMILAR VARIETY

Compared to a similar variety, 'Tan06225' (U.S. Plant Patent Pending application Ser. No. 14/121,999), which has a flower color of violet turning to light blue, 'Tan07891' has a pink flower color.

BRIEF DESCRIPTION OF THE ILLUSTRATIONS

The accompanying illustrations of FIGS. 1-7 show typical specimens of the vegetative growth and flowers of this new variety in different stages of development, depicted in color as nearly true as it is reasonably possible to make the same in a color illustration of this character; wherein.

DETAILED BOTANICAL DESCRIPTION

Figure 1:
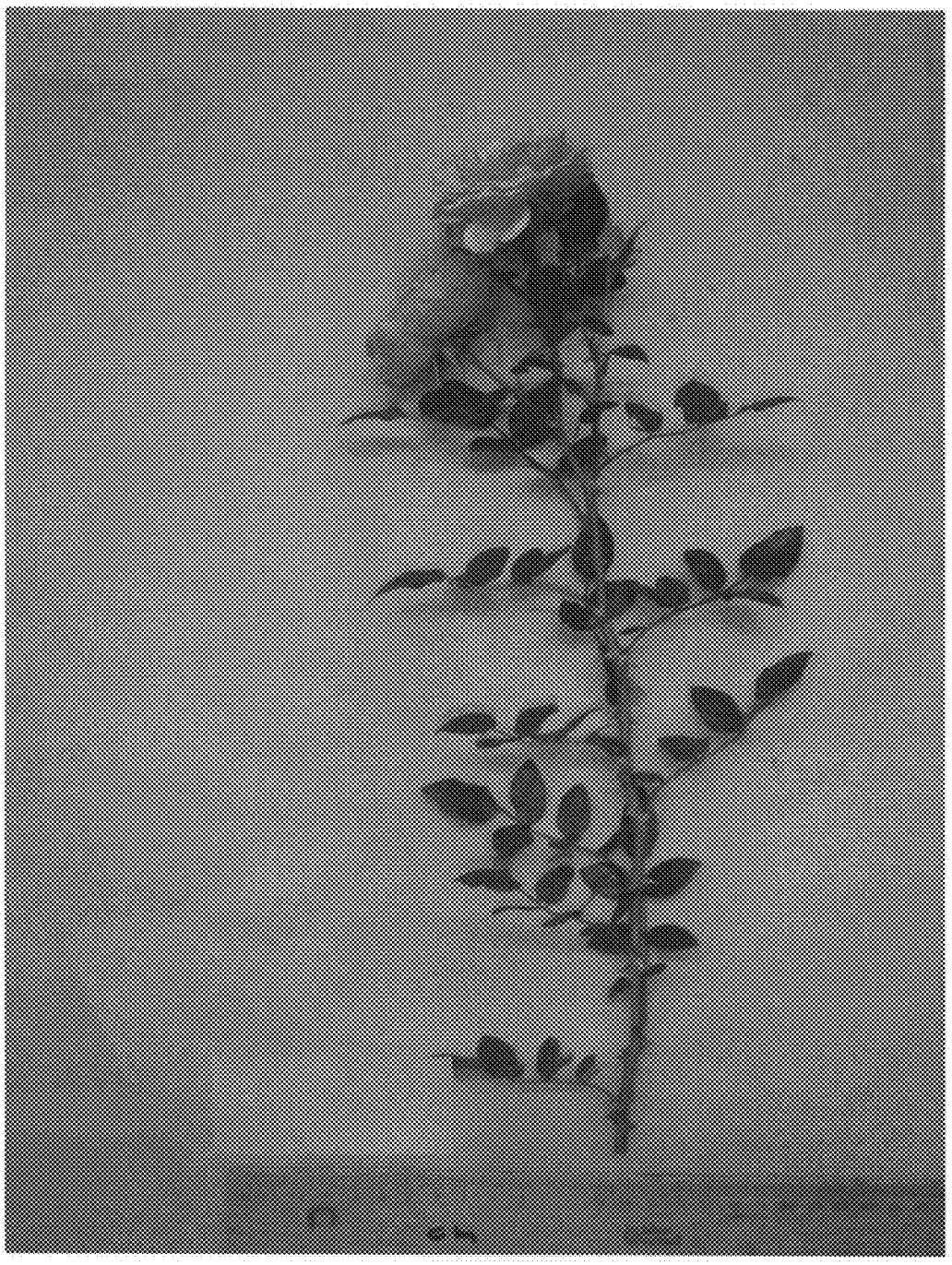
FIG. 1 is a photograph of a branch, foliage and flowers of the new variety.
Figure 2:
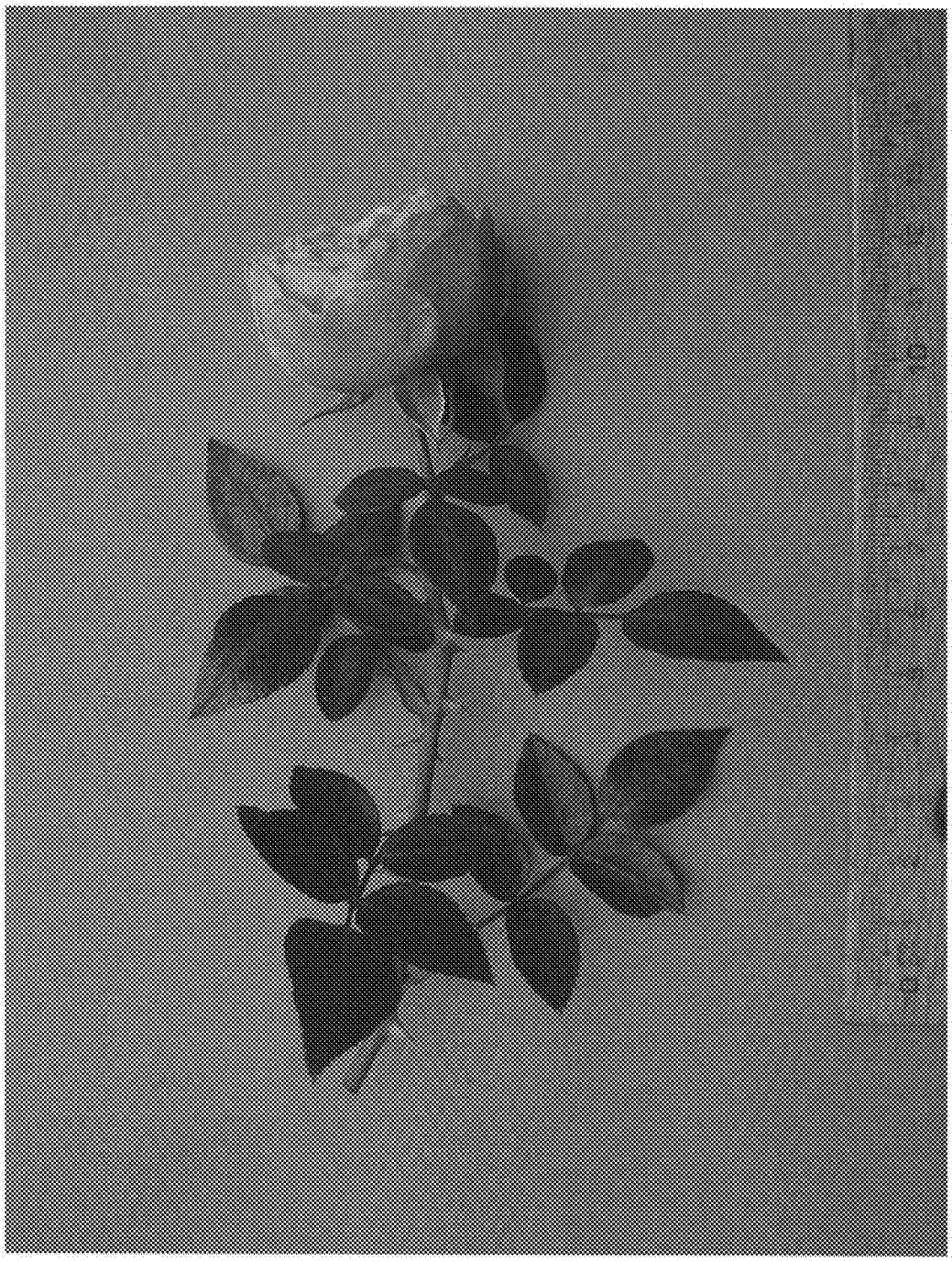
FIG. 2 is a photograph of a flower and foliage of the new variety.
Figure 3:
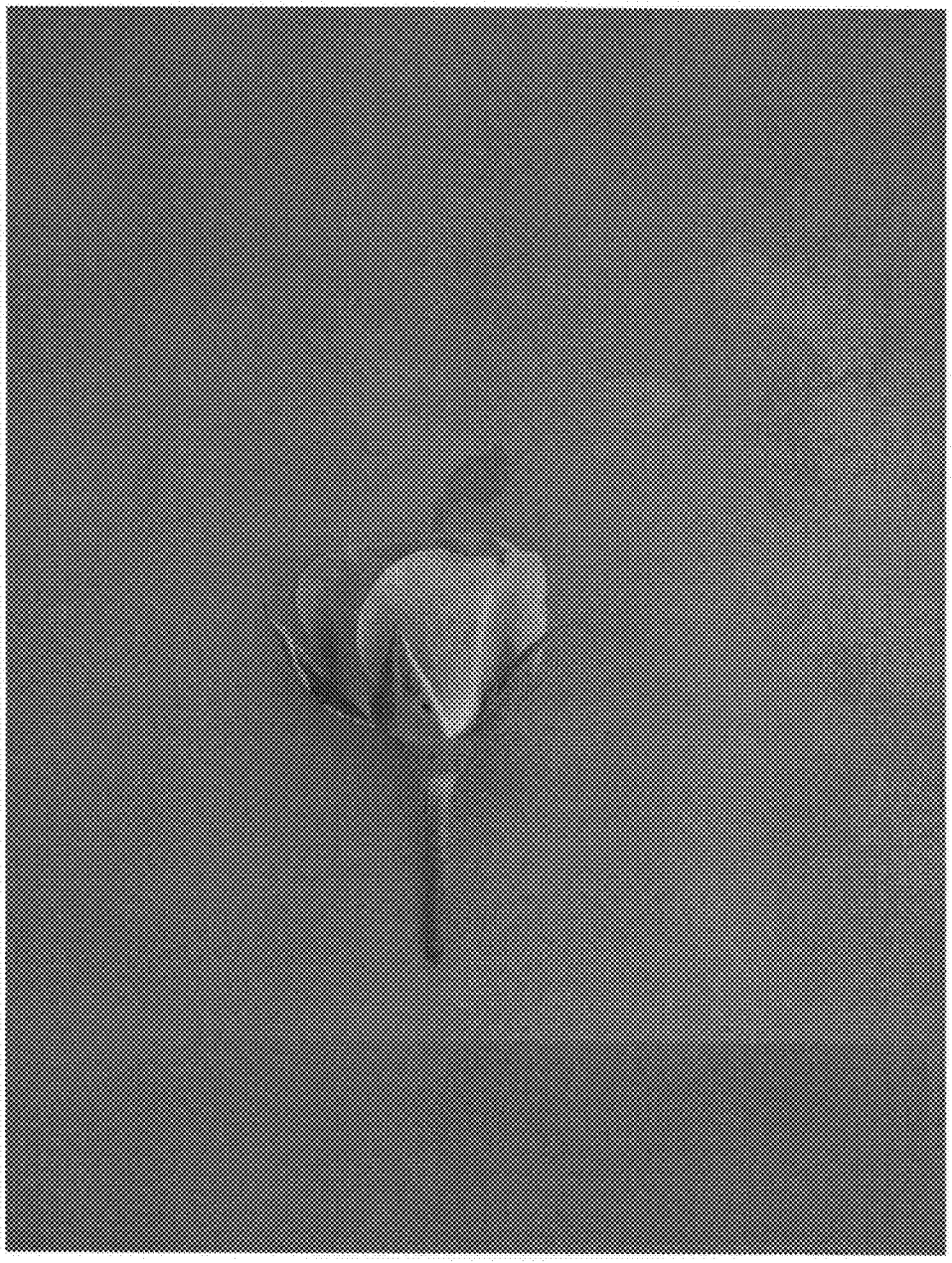
FIG. 3 is a photograph of a partially open bud of the new variety.
Figure 4:
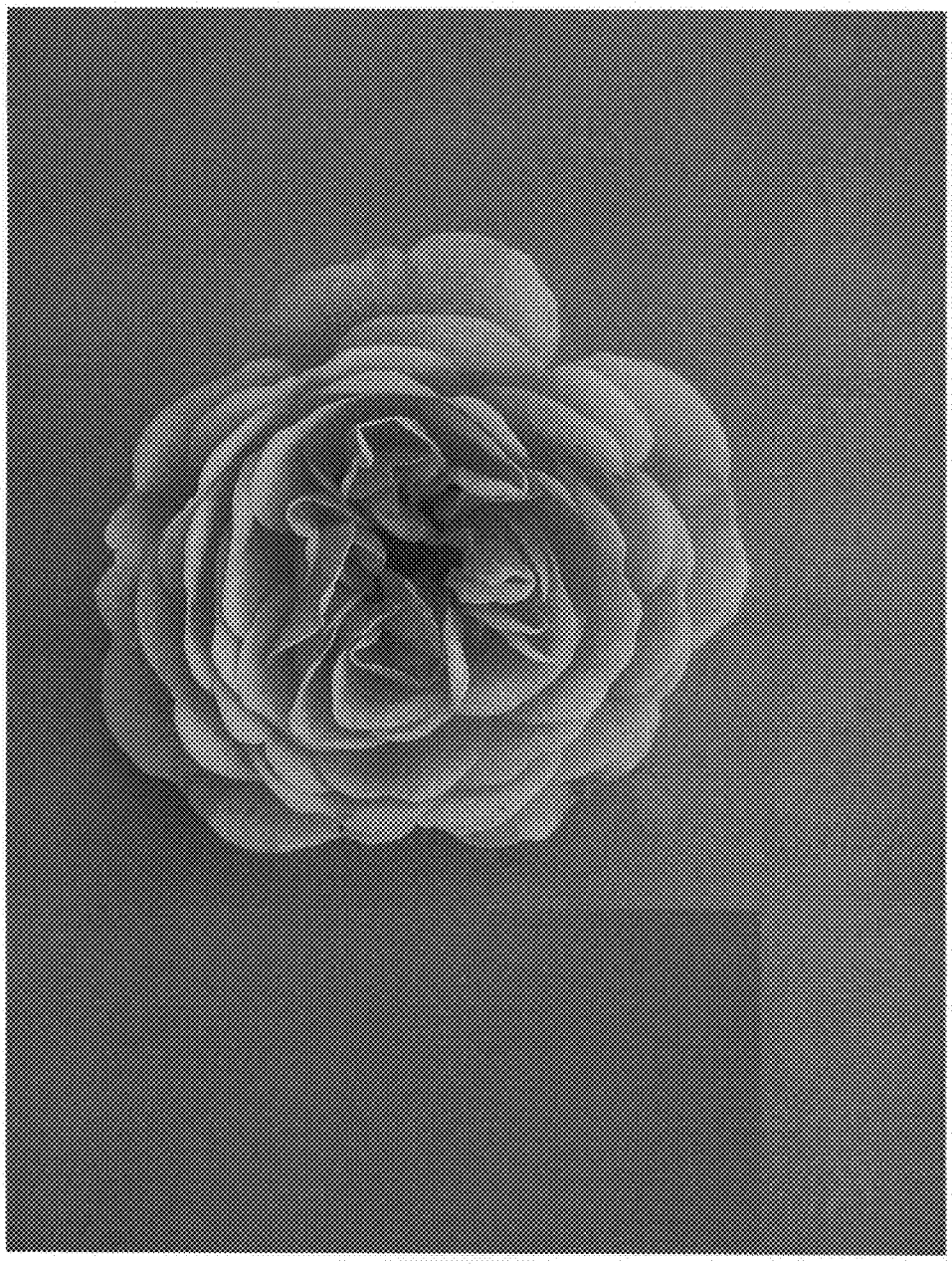
FIG. 4 is a photograph of an open flower of the new variety.
Figure 5:
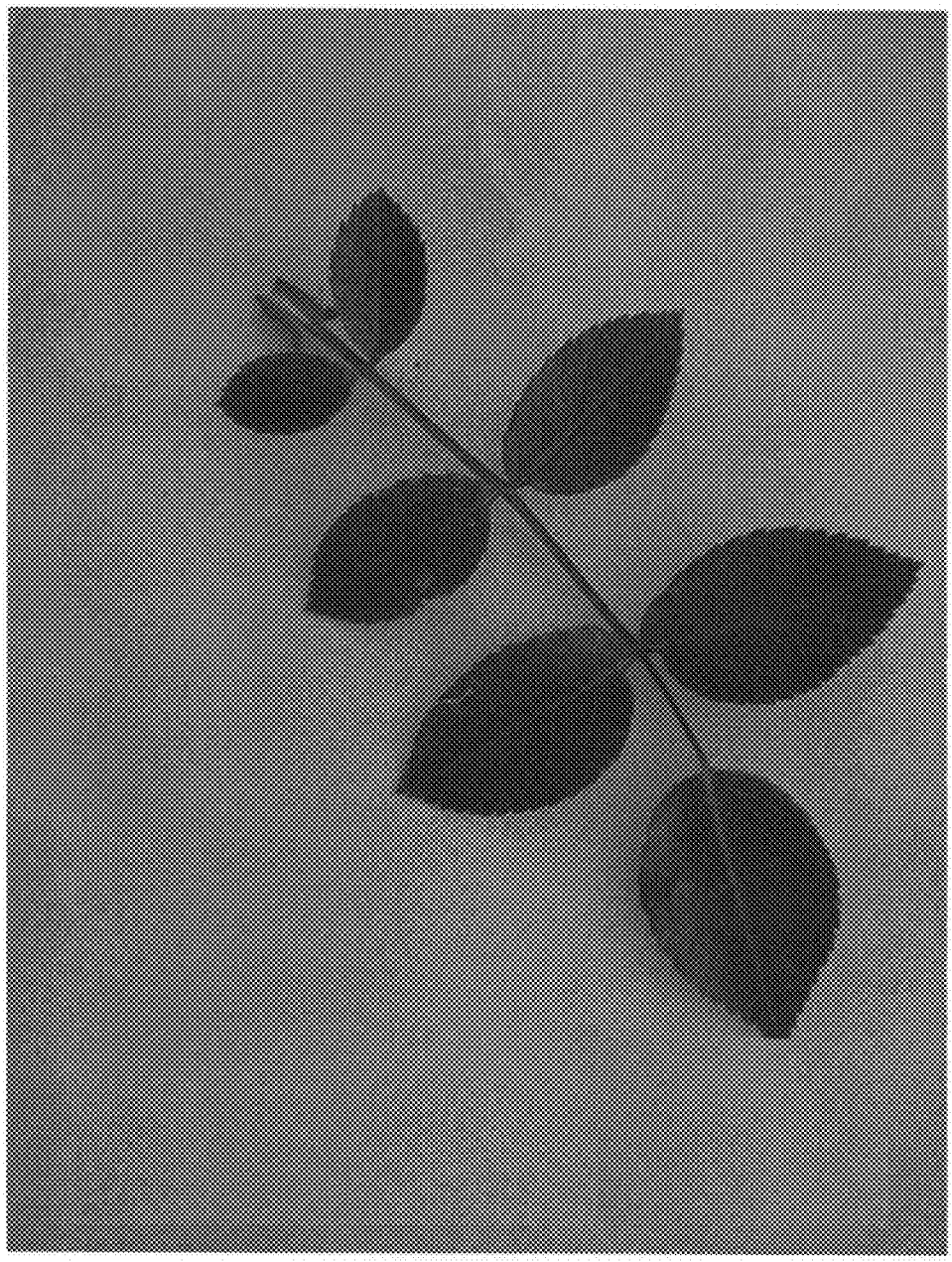
FIG. 5 is a photograph of the adaxial surface of a leaflet of the new variety.
Figure 6:
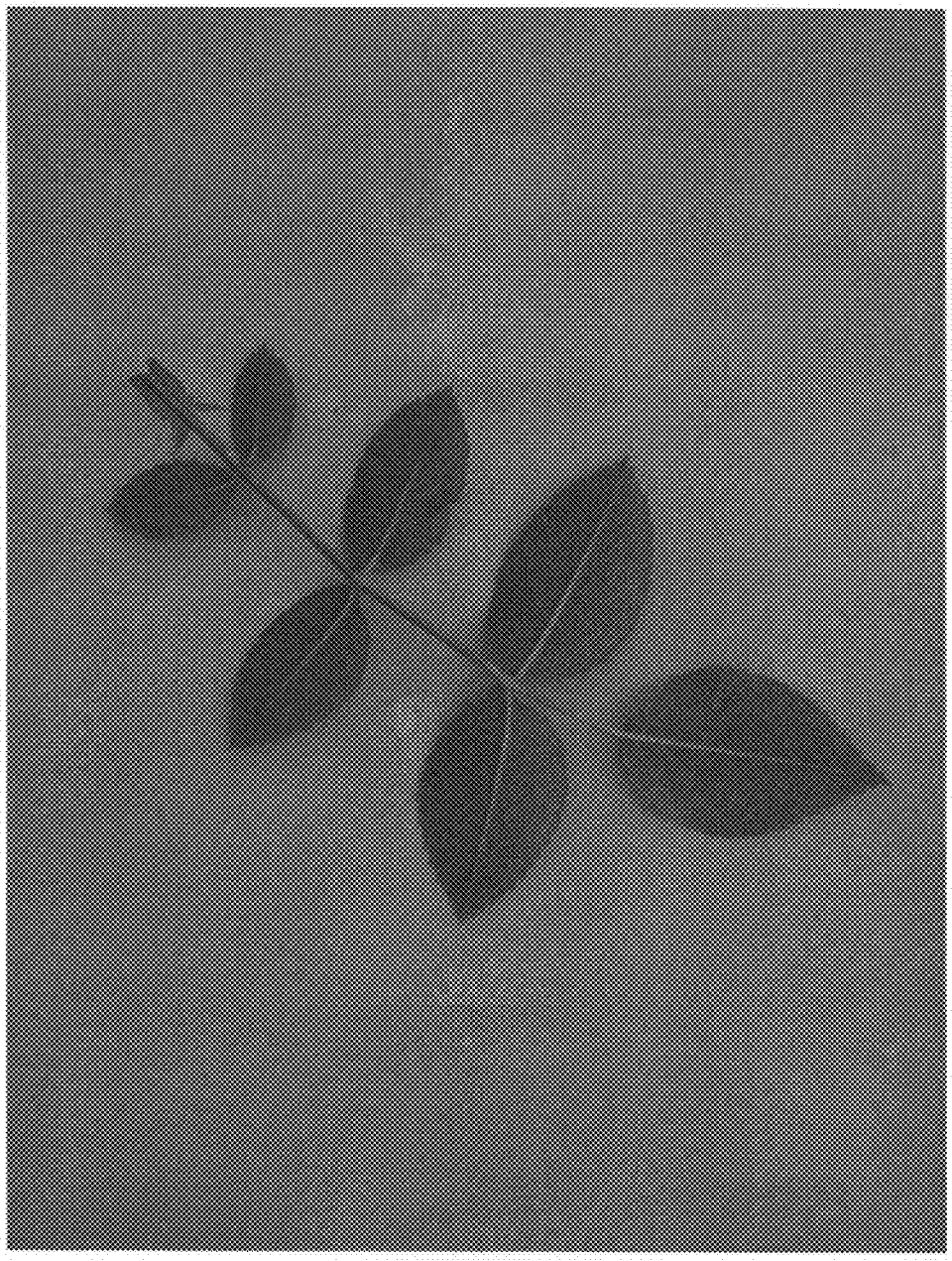
FIG. 6 is a photograph of the abaxial surface of a leaflet of the new variety.
Figure 7:
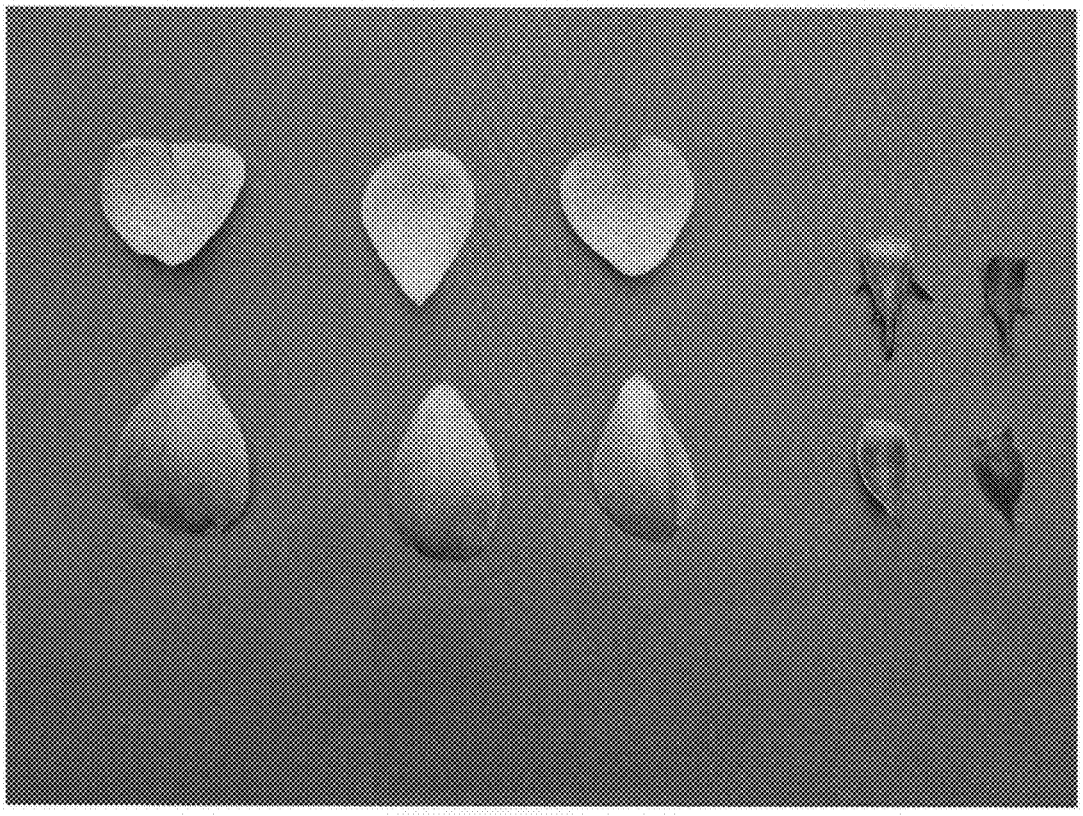
FIG. 7 is a photograph of flower petals and sepals from the new variety.

The following is a detailed description of my new rose cultivar with color descriptions using terminology in accordance with The Royal Horticultural Society (London) Colour Chart (1966), except where ordinary dictionary significance of color is indicated. Observations made from two year old plants being grown outdoors in a garden environment at Uetersen, Germany.

Parentage:

*Seed parent.*—'Hobby RT92165'.

*Pollen parent.*—'Leonardo da Vinci'.

FLOWER

Blooming habit: Continuous.

Bud:

*Size.*—About 2.0 cm long and 1.5 cm in diameter when the petals start to unfurl.

*Form.*—The bud form is short globular.

*Color.*—When sepals first divide, bud color is Red RHS 53C. When half blown, the upper sides of the petals are Red RHS 54A; and the lower sides of the petals are Red RHS 53D.

*Sepals.*—Color: Upper surface: Green RHS 141C. Lower surface: Green RHS 141D. Length: 1.8 cm. Width: 0.8 cm. Shape: Lanceolate. Surface texture: Smooth. There are three lightly appendaged sepals.

*Receptacle.*—Color: Green RHS 141D. Shape: Funnel. Size: Small, about 5 cm long×5 cm wide. Surface: Smooth.

*Peduncle.*—Length: Medium, averaging about 4.5 cm. Surface: Prickly. Color: Green RHS 141D. Strength: Erect.

Bloom:

*Size.*—Medium. Average open diameter is about 5 cm to 6 cm.

*Borne.*—Many double flowers, many umbels.

*Stems.*—Strength: Normal. Average length is about 50 cm with a diameter of 0.5.

*Form.*—When first open: Bloom is flat. Permanence: Outer petal edges curl slightly.

*Petalage.*—Number of petals under normal conditions: 64 to 72.

*Color.*—The upper sides of the petals are Red-Purple RHS 65B. The reverse sides of the petals are Red-Purple RHS 65A. The base of each petal has Red-Purple RHS 65D. The major color on the upper side is Red-Purple RHS 62B. When flower opens the color turns to a more and more light pink.

*Discoloration.*—The general tonality at the end of the first day: Red-Purple RHS 65B. At the end of the third day: Red-Purple RHS 65B. Color change with further aging: Fading to Red-Purple RHS 62D.

*Fragrance.*—None.

Petals:

*Thickness.*—Thin.

*Shape.*—Oval.

*Surface.*—Smooth.

*Margin.*—Smooth. Apex Shape: Obovate. Base Shape: Rounded.

*Form.*—Flat, tips slightly recurved.

*Arrangement.*—Regular.

*Petaloids.*—Number: 1. Color: Red-Purple RHS 65B.

*Persistence.*—Petals drop off cleanly before drying.

*Lastingness.*—On the plant: Long, about 22 days in the German climate where observed. As a cut flower: Not tested.

Reproductive parts:

*Stamens.*—Number: 32. Length: 0.5 cm. Anthers: Length: 0.1 cm. Color: Light Green RHS 145C. Arrangement: Regular around styles. Filaments: Color: Light Green RHS 145D. Length: 0.4 cm. Pollen: Color: Orange RHS 24C.

*Pistils.*—Number: 12. Length: 0.3 cm. Styles: Color: Orange RHS 24D. Length: 0.25. Stigmas: Color: Yellow RHS 11C. Length: 0.05 cm.

*Hips.*—Color: Orange RHS 24D. Shape: Round. Size: Medium, 0.7 cm.

PLANT

*Form.*—Climbing.

*Growth.*—Medium.

*Age at maturity.*—4 years.

*Mature plant.*—Height: Typical — 150 cm to 200 cm. Width: Typical — 50 cm.

*Rootstock.*—Propagated by cuttings.

Foliage: Number of leaflets on normal mid-stem leaves: 5.

*Size.*—About 7.2 cm long×4.9 cm wide.

*Quantity.*—Abundant.

*Color.*—New foliage: Upper side: Red RHS 53A. Lower side: Greyed-Orange RHS 177A. Old foliage: Upper side: Green RHS 137A. Lower side: Green RHS 138B.

Leaflets:

*Size.*—About 2.7 cm long×1.5 cm wide.

*Shape.*—Pointed oval.

*Base shape.*—Rounded.

*Apex shape.*—Pointed.

*Texture.*—Leathery.

*Edge.*—Serrated.

*Serrations.*—Single.

*Petiole.*—Color: Green RHS 138B.

*Petiole rachis.*—Color: Red RHS 36C. Underside: Rough.

*Auricle shape.*—None.

*Stipules.*—Length: 1.3 cm, serrated.

*Disease resistance.*—Under normal growing conditions: Mildew: Resistant. Blackspot: Resistant. Rust: Resistant.

*Pest resistance.*—Average.

*Vein color.*—Yellow-Green RHS 145C.

*Venation pattern.*—Pyramidal.

Wood:

*New wood.*—Color: Green RHS 146D. Bark: Smooth.

*Old wood.*—Color: Greyed-Orange RHS 165A. Bark: Rough.

Prickles:

*Quantity.*—On main canes from base: 27 per 30 cm. On laterals from main canes: Ordinary.

*Form.*—Hooked downward.

*Length.*—0.6 cm.

*Color when young.*—Greyed-Orange RHS 166B.

*Color when mature.*—Red RHS 47A.

Small prickles:

*Quantity.*—On main stalks: Few. On laterals: Few.

*Color.*—Red RHS 47A.

Winter hardiness: Hardy to Zone 7A.

I claim:

1. A new and distinct variety of rose plant climbing rose plant, substantially as herein illustrated and described.

* * * * *